United States Patent [19]

Sato et al.

[11] 4,385,892
[45] May 31, 1983

[54] SETTING COMPOSITIONS FOR DENTAL PURPOSES

[75] Inventors: Atsushige Sato, No. 24-3, 4-chome, Asagayakita, Suginame-ku, Tokyo; Ishi Miura, No. 21-6, 3-chome, Kamimeguro, Meguro-ku, Tokyo, both of Japan; Yasuhiro Kumei, Tokyo, Japan; Osamu Okuno, Narashino, Japan; Bunsaku Yoshida, Warabi, Japan

[73] Assignees: Atsushige Sato; Ishi Miura; G-C Dental Industrial Corp., all of Tokyo, Japan

[21] Appl. No.: 356,443

[22] Filed: Mar. 9, 1982

[30] Foreign Application Priority Data

Mar. 20, 1981 [JP] Japan ................................. 56-39575

[51] Int. Cl.³ .............................................. A61K 6/08
[52] U.S. Cl. ..................................... 433/228; 106/35; 420/501; 420/503; 420/504; 420/505; 420/506; 420/527; 433/226

[58] Field of Search .................. 106/35; 433/228, 226; 420/501, 503, 504, 505, 506, 527

[56] References Cited

U.S. PATENT DOCUMENTS

| 1,803,386 | 5/1931 | Fischer et al. | 433/228 |
| 4,008,073 | 2/1977 | Kropp | 420/501 |
| 4,064,629 | 12/1977 | Stoner | 433/226 |

Primary Examiner—Lorenzo B. Hayes
Attorney, Agent, or Firm—Oblon, Fisher, Spivak, McClelland & Maier

[57] ABSTRACT

A novel setting composition for dental purposes comprises a dental silver amalgam alloy composed mainly of silver and tin, and including one or more of copper, zinc, indium, palladium and gold; mercury in an amount sufficient to amalgamate said alloy: and selenium. The selenium may or may not be coated with a metal showing an affinity for mercury, such as silver. The amount of selenium contained is in a range of 0.005 to 5% by weight.

7 Claims, 4 Drawing Figures

SETTING COMPOSITIONS FOR DENTAL PURPOSES

BACKGROUND OF THE INVENTION

The present invention relates to dental amalgam compositions.

The dental amalgams are prepared by tritulating alloy powders composed mainly of silver and tin with mercury, and condensed and set into the cavities of the teeth in the mouth.

In what follows, all the percent refers to % by weight unless otherwise noted. Heretofore, the alloys for the dental amalgam have been composed mainly of silver, 65% min., tin, 29% max., mercury, 3% max., and zinc, 2% max., as specified by JIS T-6109. However, it has been found that such amalgam alloys meeting the specification have insufficient mechanical properties and corrosion resistance, since, once set, a phase of $Sn_{7-8}Hg$ ($\gamma_2$) is crystallized out, which is poor in strength and susceptible to corrosion.

Recently, it has been proposed to use the high-copper or dispersion-strengthened type of amalgam alloys which cause no crystallization of such a phase. These alloys include copper in an amount exceeding the upper limit provided by the foregoing Japanese Industrial Standards (JIS), and have been come up with to make improvements in mechanical properties by causing crystallization of $Cu_3Sn$ ($\epsilon$) or $Cu_6Sn_5$ ($\eta$) phase, while suppressing crystallization the $Sn_{7-8}Hg$ ($\gamma_2$) phase. However, these proposals have taken no care of initial compressive strength after condensation and the toxicity of the leaching mercury. In other words, it takes several hours to make the condensed amalgam reach a strength sufficient to resist biting forces; in the meantime, there is a possibility that the condensed amalgam may break due to external forces, if applied. To add to this, the conventional amalgam has another disadvantage in that, during setting, it comes in contact with oral fluids, so that the harmful mercury leaches and accumulate in the body.

SUMMARY OF THE INVENTION

A main object of the present invention is to provide a solution to the above-mentioned problems.

It has now been found that an element selenium is effective in increasing the initial compressive strength of a dental amalgam to prevent it from breaking due to biting forces and in suppressing the toxicity of the leaching mercury.

Selenium is an element difficult to form an alloy with amalgamable elements, silver, tin, copper, mercury etc.; still, it reacts partly with mercury in an amalgam to provide a phase of SeHg. That reaction takes place only in the surface layer of the amalgam, however, This results in a lowering of the plasticity of the amalgam increases in the initial compressive strength thereof. This mechanism is considerably similar to that of concrete comprising pieces of stone, sand and cement, and provides an extremely firm structure. As a consequence, once set, the amalgam has improved mechanical properties such as compressive strength and flow. The most unique effect that selenium possesses is that it is antagonistic to the toxicity of the mercury leaching in oral fluids.

Thus, the present invention provides a setting composition for dental purposes comprising a dental amalgam alloy composed mainly of silver and tin and one or more of copper, zinc, indium, palladium and gold; mercury in an amount sufficient to amalgamate said alloy; and selenium.

BRIEF EXPLANATION TO THE FIGURES

FIG. 1 shows the normal cultured L cells.

FIG. 2 shows the L cells applied with the amalgam of comparison sample 1.

FIG. 3 shows the L cells applied with the amalgam of sample 3.

FIG. 4 shows the L cells applied with the amalgam of sample 1.

DETAILED EXPLANATION OF THE INVENTION

Figure 1:
FIGS. 1–4 show the phase contrast microphotograph of the L cells.

The amount of selenium contained in the amalgam composition according to the present invention is 0.005 to 5% relative to the total weight of the amalgam alloy and the mercury to amalgamate it. The upper limit of 5% is placed for the reasons that, in amounts above said value, the resulting composition is inferior in compressive strength to a selenium-free composition, whereas the lower limit of 0.005% is done for the reasons that, in amounts below said value, selenium is found to show no substantial effect.

The amalgam compositions contain selenium are applicable with equal advantages not only to the conventional alloys meeting the Japanese Industrial Standards but also to the dispersion-strengthened type or the high-copper type of alloys. Selenium may be contained in an amalgam mixture in any suitable manner by, e.g., (i) mixing selenium with powders of an amalgam alloy followed by tritulating with mercury; (ii) pre-melting selenium in an amalgam alloy or mercury from one or both of which is obtained an amalgam and (iii) mixing selenium-containing alloy powders of dispersion type and mercury. The selenium thus added has an effect on improvements in the initial compressive strength of the amalgam and reductions in the toxicity of mercury.

In a particularly preferred method for the addition of selenium, the selenium powders are pre-coated by vapor-deposition or plating with any one of silver, tin, copper, zinc, indium, palladium, gold and mercury or an alloy of one or more of these metals. This method makes amalgamation more uniform than do the above-mentioned three methods in which selenium is merely added, and hence renders into practice of the present invention more effective.

The present invention will now be explained with reference to the following non-restrictive examples and comparison examples, in which samples are prepared as described later, and then subjected to testing.

EXAMPLE 1

An amalgam alloy having a composition of silver 70%, tin 27% and copper 3% was melted and disintegrated by atomization in a nitrogen stream. The fine powders, which passed through a sieve of 270 meshes, were heat-treated, and then mixed uniformly with 0.2% by weight of selenium powders. The resulting mixture was added with mercury in a weight ratio of 1 to 0.75, and tritulated mechanically by means of an amalgamator for ten seconds to prepare a sample 1.

EXAMPLE 2

An amalgam alloy having a composition of silver 70%, tin 27% and copper 3% was melted and disintegrated by atomization in a nitrogen stream. The fine powders, which passed through a sieve of 270 meshes, were heat-treated, and then mixed uniformly with 0.2% by weight of selenium powders which had been precoated by vacuum-deposition with silver thin layers having a thickness of about five micronmeters. The resulting mixture was added with mercury in a weight ratio of 1 to 0.75, and triturated mechanically by means of an amalgamator for ten seconds to prepare a sample 2.

EXAMPLE 3

An amalgam alloy having a composition of silver 70%, tin 26%, copper 3%, zinc 0.5% and selenium 0.5% was melted, and poured into a mold to obtain an ingot which was in turn lathed. The fine powders, which passed through a sieve of 200 meshes, were heat-treated. The resulting mixture was added with mercury in a weight ratio of 1 to 1, and triturated mechanically by means of an amalgamator for ten seconds to prepare a sample 3.

EXAMPLE 4

An amalgam alloy having a composition of silver 60%, tin 27% and copper 13% was melted and disintegrated by atomization in a nitrogen stream. The fine powders, which passed through a sieve of 270 meshes, were heat-treated, and added with 0.1% selenium-containing mercury in a weight ratio of 1 to 0.85. The resulting mixture was mechanically triturated by means of an amalgamator for ten seconds to prepare a sample 4.

EXAMPLE 5

An amalgam alloy having a composition of silver 69.9%, tin 27%, copper 3% and selenium 0.1% was melted and disintegrated by atomization in a nitrogen stream. The fine powders, which passed through a sieve of 270 meshes, were heat-treated, and added with 0.1% selenium-containing mercury in a weight ratio of 1 to 0.75. The resulting mixture was mechanically triturated by means of an amalgamator for ten seconds to prepare a sample 5.

EXAMPLE 6

An amalgam alloy having a composition of silver 70%, tin 27%, copper 2% and selenium 1% was melted and poured into a mold to prepare an ingot which was in turn lathed. The first fine powders, which passed through a sieve of 200 meshes, were heat-treated. The powders were mixed mechanically with the second fine powders in a weight ratio of 6 to 4, said second fine powders being obtained by melting an amalgam alloy having a composition of silver 72%, copper 27% and indium 1% followed by atomization and sieving with a sieve of 270 meshes. The resulting powders were added with mercury in a weight ratio of 1 to 1.2, and triturated mechanically by means of an amalgamator for 15 seconds to prepare a sample 6.

EXAMPLE 7

An amalgam alloy having a composition of silver 45%, tin 30% and copper 25% was melted and disintegrated by atomization in a nitrogen stream. The fine powders, which passed through a sieve of 270 meshes, were heat-treated and added with mercury in a weight ratio of 1 to 0.82. The resulting mixture was added with selenium powders in an amount of 2.0% relative to the total weight of the alloy powders and mercury, and tritulated mechanically by means of an amalgamator for ten seconds to prepare a sample 7.

Reference will now be made to comparison examples in which selenium is not contained, for the purpose of comparison.

COMPARISON EXAMPLE 1

An amalgam alloy having a composition of silver 70%, tin 27% and copper 3% was melted and disintegrated by atomization in a nitrogen stream. The fine powders, which passed through a sieve of 270 meshes, were heat-treated, and added with mercury in a weight ratio of 1 to 0.75. The resulting mixture was mechanically triturated by means of an amalgamator for ten seconds to prepare a comparison sample 1.

COMPARISON EXAMPLE 2

An amalgam alloy having a composition of silver 70%, tin 26%, copper 3% and zinc 1% was melted and poured into a mold to obtain an ingot which was then lathed. The fine powders, which passed through a sieve of 200 meshes were heat-treated, and added with mercury in a weight ratio of 1 to 1. The resulting mixture was mechanically triturated by means of an amalgamator for ten seconds to prepare a comparison sample 2.

COMPARISON EXAMPLE 3

An amalgam alloy having a composition of silver 70%, tin 27% and copper 3% was melted and poured into a mold to obtain an ingot which was then lathed. The fine powders, which passed through a sieve of 200 meshes, were heat-treated. Apart from this, an amalgam alloy having a composition of silver 72%, copper 27% and indium 1% was melted and disintegrated by atomization in a nitrogen stream, followed by sieving with a sieve of 270 meshes. The first powders were mechanically mixed with the second powders in a weight ratio of 6 to 4 to form alloy powders which were added with mercury in a weight ratio of 1 to 1.2. The resulting mixture was mechanically triturated by means of an amalgamator for 15 seconds to prepare a comparison sample 3.

TABLE

| | Manipulation time (min) | Compressive Strength (Kg/cm$^2$) | | Flow (%) | Cytotoxicity * |
|---|---|---|---|---|---|
| | | 30 min. | 24 hours | | |
| Sample 1 | 8 | 637 | 4750 | 0.73 | None |
| Sample 2 | 8 | 933 | 5070 | 0.70 | None |
| Sample 3 | 6 | 710 | 4010 | 2.30 | Slight |
| Sample 4 | 6 | 967 | 6160 | 0.31 | None |
| Sample 5 | 8 | 625 | 4650 | 1.20 | None |
| Sample 6 | 6 | 765 | 5530 | 1.05 | None |
| Sample 7 | 8 | 772 | 5180 | 0.58 | Slight |
| Comparison Sample 1 | 8 | 403 | 4340 | 1.42 | Marked |
| Comparison Sample 2 | 6 | 445 | 3770 | 2.80 | Marked |
| Comparison Sample 3 | 6 | 534 | 5281 | 1.60 | Marked |

* See FIGS. 1 to 4

In the table, the manipulation time shall be taken as a period of time during which the samples are condensed and easily carved in the tooth model, and both the compressive strength and the flow were measured according to the American Dental Association Specification No. 1 (A. D. A. S. No. 1).

Testing on the cytotoxicity was carried out on the basis of Spangberg's 51Cr release assay.

The test results indicate that Samples 1, 2, 5 and 7, although the manipulation time is identical with Comparison Sample 1, have their compressive strength after 30 min. about 1.5 to 2 times compared with that of Comparison Sample 1. This means that Samples 1, 2, 5 and 7 are advantageously prevented from breaking due to initial biting forces which may be applied after condensing. In addition, the inventive samples continued to increase in compressive strength even after 24 hours, so that the flow was disincreased. This means that the inventive samples provide condensed restorations which can resist to biting forces over extended period of time and, hence, are not possibly broken. Similar results are obtained if Samples 3 and 6 are compared with Comparison Sample 2 and 3, respectively.

Example 2 shows the effect that is obtained by the selenium pre-coated with a metal showing an affinity for mercury. From a comparison between Sample 2 and Sample 1, it is found that the former is in its initial compressive strength after 30 min. about 1.5 times compared with that of the latter. Sample 2 increases its high final strength. Thus, the selenium coated in advance with a metal showing an affinity for mercury, such as silver, permits earlier uniform amalgamation with extremely little virtual fear of breaking of the condensed restoration at the initial biting.

The cytotoxicity tests reveal that Samples 1-2 and 4-6 show no toxicity at all, and samples 3 and 7 show a slight degree of toxicity, whereas Comparison Samples 1-3 all shows a considerable degree of toxicity.

Typical results of the toxicity tests are shown in FIGS. 1-4.

Figure 2:
Figure 3:
Figure 4:
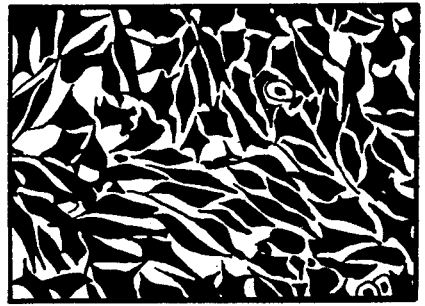

More specifically, FIG. 1 is a phase contrast microphotograph of the normally cultured L cells, and FIG. 2 is a similar photograph of the L cells to which Comparison Sample 1 was applied, showing that all the cells are exterminated. FIG. 3 shows the cells to which Sample 3 was applied, showing that the cell density decreases slightly, yet the cell shape is similar to that of the normal cells, and hence the cytotoxicity is reduced. FIG. 4 shows the cells to which Sample 1 was applied, showing that the cell density and shape are comparable to those of the normal cells and, hence, the cytotoxicity are completely eliminated.

It is thus found that the selenium-containing amalgam shows no or extremely little cytotoxicity as compared with the selenium-free amalgam, and provides condensed restorations well-suited to oral conditions.

As will be appreciated from the foregoing, the dental amalgams according to the present invention are superior to the prior art amalgams not only are mechanical properties improved but also the cytotoxicity is reduced or eliminated. The inventive compositions have no or extremely little cytotoxicity.

What we claim is:

1. A setting composition for dental purposes comprising a dental silver alloy composed mainly of silver and tin, and including one or more of copper, zinc, indium, palladium and gold; mercury in an amount sufficient to amalgamate said alloy; and selenium.

2. A setting composition of claim 1, in which selenium is coated with one or more of said alloy ingredients.

3. A setting composition of claim 1 or 2, in which the amount of selenium contained is in a range of 0.005 and 5% by weight.

4. A setting composition of claim 1, in which said alloy contains selenium.

5. A setting composition of claim 1 or 4, in which said alloy contains mercury in an amount of no more than 3% by weight.

6. A setting composition of claim 1, 2 or 4, in which selenium is contained in the mercury to amalgamate said alloy.

7. A setting composition of claim 1, 2 or 4, in which selenium is present in both said alloy and said mercury for amalgamation.

* * * * *